United States Patent [19]
Wang

[11] Patent Number: 4,895,650
[45] Date of Patent: Jan. 23, 1990

[54] MAGNETIC SEPARATION RACK FOR DIAGNOSTIC ASSAYS

[75] Inventor: Robert Wang, San Diego, Calif.

[73] Assignee: Gen-Probe Incorporated, San Diego, Calif.

[21] Appl. No.: 160,551

[22] Filed: Feb. 25, 1988

[51] Int. Cl.$^4$ ............................................... B03C 1/02
[52] U.S. Cl. .................................... 210/222; 422/101; 422/104; 436/809
[58] Field of Search ......................... 210/222, 223, 695; 422/101, 104; 436/177, 525, 526, 809, 810; 335/305

[56] References Cited

U.S. PATENT DOCUMENTS

| | | | |
|---|---|---|---|
| 280,130 | 8/1985 | Harkins et al. | D24/21 |
| 3,970,518 | 7/1976 | Giaever | 195/1.5 |
| 3,985,649 | 10/1976 | Eddelman | 210/42 S |
| 4,018,886 | 4/1977 | Giaever | 424/12 |
| 4,141,687 | 2/1979 | Forrest et al. | 23/230 R |
| 4,272,510 | 6/1981 | Smith et al. | 427/47 |
| 4,438,068 | 3/1984 | Forrest | 422/61 |
| 4,793,973 | 12/1988 | Ringrose | 436/810 |

FOREIGN PATENT DOCUMENTS 209490 1/1987 European Pat. Off. ............ 436/526

OTHER PUBLICATIONS

Griffin, K. Mosbach, and R. Mosbach, Magnetic Biospecific Affinity Adsorbents for Immunoglobin and Enzyme Isolation, *Applied Biochemistry and Biotechnology* 6, 283–292(1981).

*Primary Examiner*—W. Gary Jones
*Assistant Examiner*—Matthew O. Savage
*Attorney, Agent, or Firm*—Lyon & Lyon

[57] ABSTRACT

A magnetic separation rack and method for separating magnetically attractable particles used in an assay technique such as a heterogeneous diagnostic assay. The rack has a plurality of test tubes holders and a series of magnets positioned so that each test tube has one and only one magnetic immediately adjacent thereto. The magnet is on the side of the test tube at an upper position thereof without extending to the bottom. The particles are then attracted to the side of the test tube permitting removal or rinsing of the medium.

4 Claims, 3 Drawing Sheets

MAGNETIC SEPARATION RACK FOR DIAGNOSTIC ASSAYS

BACKGROUND OF THE INVENTION

The field of the present invention is magnetic separation of solid and liquid phases. More particularly, it relates to magnetic separation useful in heterogeneous assays such as genetic probe assays and ligand-receptor assays such as immunoassays.

It is well known to assay for antigens, antibodies, polynucleotides and other target substances present in a liquid sample by reactions using a labeled reagent, the assay being affected by measuring the amount of label either bound in a complex of the target and labeled reagent bound to a solid phase or remaining unbound in solution. Various techniques for quantifying labels include, for example, radiometric, enzymatic, fluorometric, and chemiluminescent methods. In all of these procedures, it is generally necessary either to separate the complexes formed from the remainder of the reaction mixture, or to separate the free unbound labeled reactant from the remainder of the reaction mixture in order to measure the amount of label in either part. This separation step is difficult to perform cleanly and is therefor a source of error in the procedures.

Prior to quantification, it is generally necessary to separate the complexed products from the surrounding medium. One such separation technique is the use in immunoassays of magnetically attractable particles which specifically bind either the complexes formed or the unbound labeled reactant and applying a magnetic field to draw and hold the particles and allow the surrounding medium to be flushed away or removed. Such methods and devices are disclosed in U.S. Pat. Nos. 4,141,687, 4,272,510, 3,985,649 and 4,438,068. These patents may be consulted to provide background on immunoassay techniques and magnetic separation procedures.

Although existing methods and apparatus are known for the magnetic separation of solid phase immunoassays, the known procedures have limitations including specific requirements as to magnet size, magnet orientation of both magnetic axis and the north/south orientation, as well as various process constraints and inefficiencies. An improved method and device for performing magnetic separation for heterogeneous immunoassays, genetic probe assays and other assays is desired for repetitive laboratory use.

SUMMARY OF THE INVENTION

The present invention is directed to a device and method for performing multiple magnetic separations in a plurality of containers for heterogeneous assays. The device is comprised of a rack which accepts and holds the containers. A series of magnets are positioned adjacent the containers such that each container has one and only one magnet immediately adjacent thereto. Each respective magnet is located to one side of one or more containers and it does not extend to the bottom of the container.

DETAILED DESCRIPTION OF THE PREFERRED EMBODIMENT

The preferred embodiment will now be described with reference to the drawings. For convenience, a numeral representing a component in one figure will represent the same component in any other figure.

Figure 1:
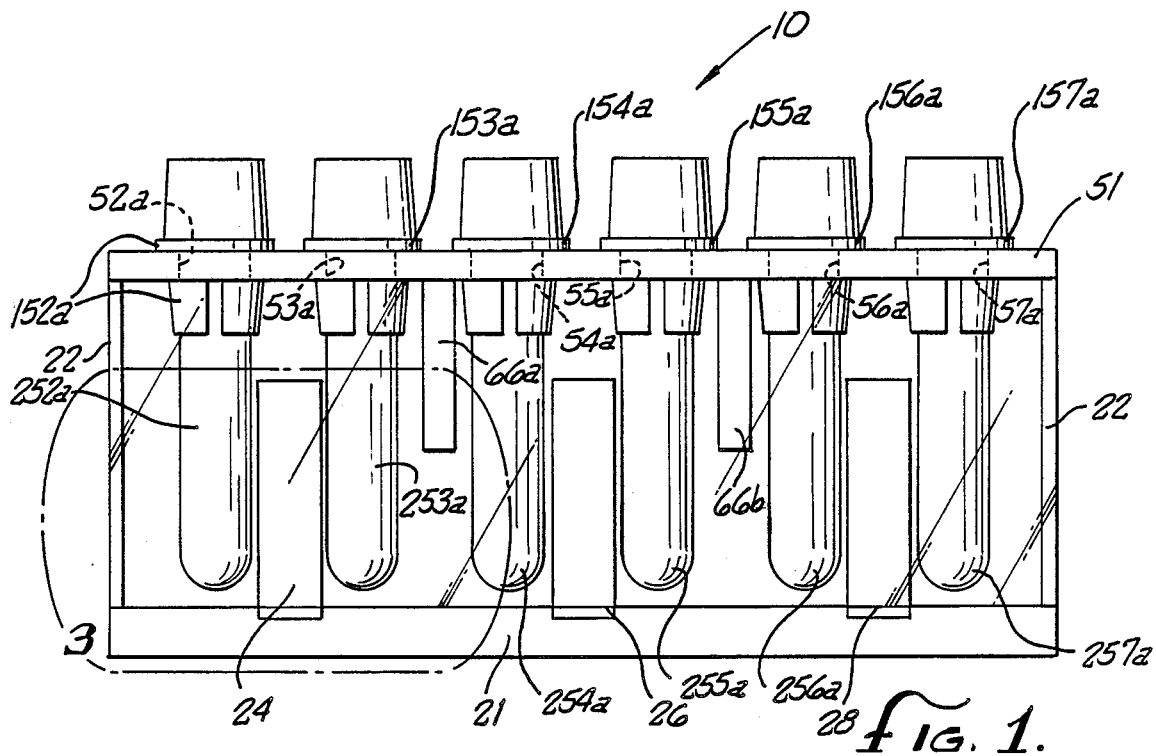
FIG. 1 is a front view.

FIG. 1 is a front view of a magnetic separation rack 10 according to the present invention. The structure of rack 10 is comprised of a rectangular base 21 having two upright sides 22, 22 attached thereto on opposite ends of the base 21. Also attached to base 21 are magnetic assemblies 24, 26, 28 which run the width of the base 21. FIG. 1 illustrates a series of test tubes 252a–257a held and secured by respective aperature inserts 152a–157a within the holes or apertures (shown in FIG. 2) within a top 52a–57a surface 51.

Figure 2:
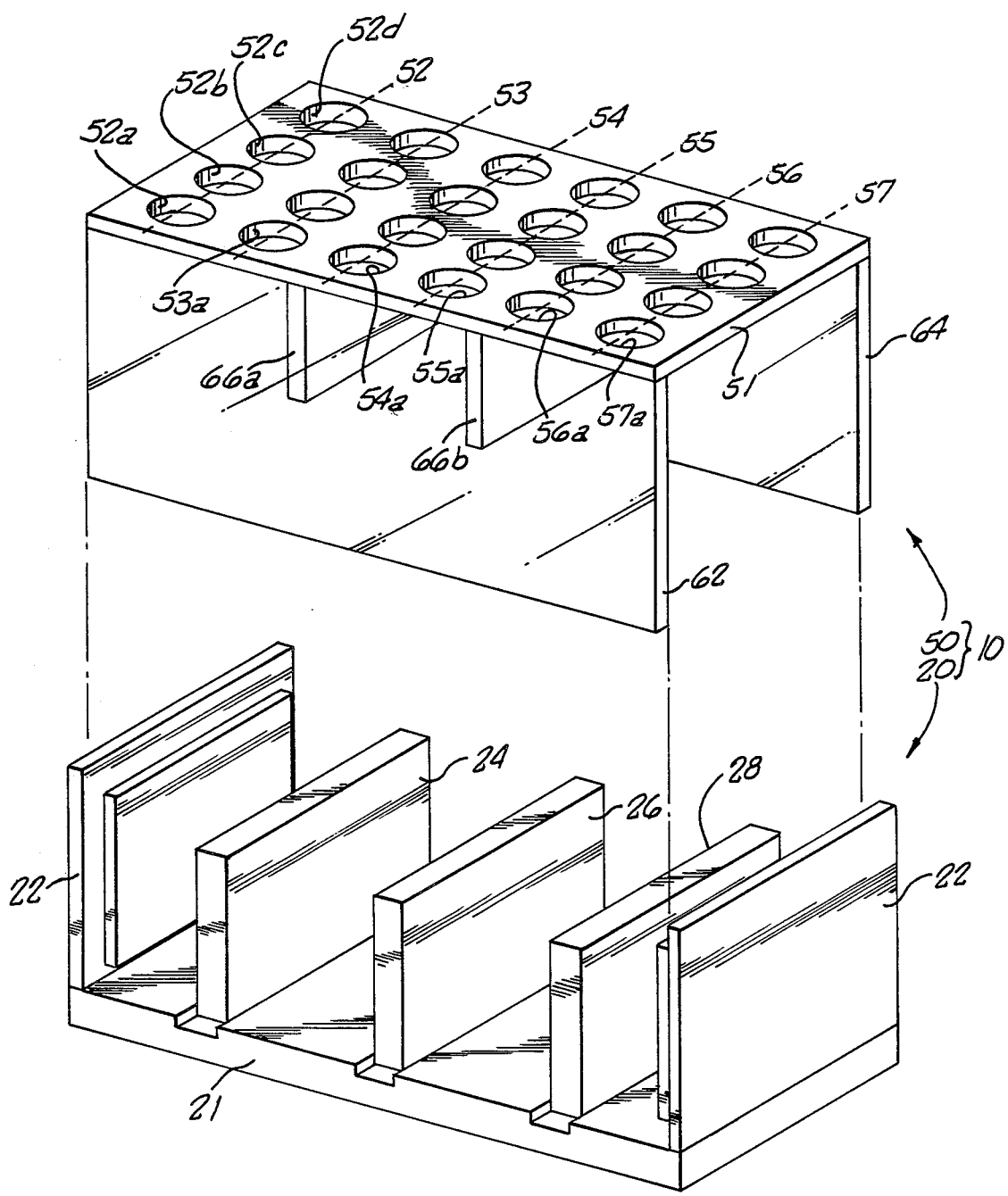
FIG. 2 is an exploded perspective view of a magnetic separation rack according to the present invention.

As best illustrated in the exploded view of FIG. 2, rack 10 is comprised of a bottom portion 20 and a top portion 50. Top portion 50 is comprised of the top surface 51 having a plurality of apertures therethrough. The apertures are arranged in rows (e.g., 52a–d). Top surface 51 is shown having six aperture rows 52, 53, 54, 55, 56, 57 each having four apertures or holes (e.g., 52a–d, 53a–d, etc.) therein. Open on either end, top portion 50 has a front face 62 and a back face 64. Support braces 66a, 66b are connected between the parallel and opposing front face 62 and back face 64 to provide stability and support for the top portion 50. Support braces 66a, 66b are located in the spaces or aisles between adjacent rows of apertures. Support brace 66a is between aperture rows 53 and 54 and support brace 66b is between rows 55 and 56.

Bottom portion 20 has a rectangular base 21 having a length which is approximately 50% longer than its width. Attached to the width ends of base 21 are upright sides 22, 22. Also attached to base 21 are magnetic assemblies 24, 26, 28 which are illustrated as rectangular plates attached to base 21 and running the width thereof. Magnetic assemblies 24, 26, 28 have parallel faces and are equally spaced in the spaces or aisles between consecutive rows of apertures (e.g., 52a–d and 53a–d) in top surface 51. The magnetic assemblies 24, 26, 28 are positioned in alternating aisles so that each aperture is adjacent to one and only one magnetic assembly. When assembled, magnetic assembly 24 is between rows 52 and 53, magnetic assembly 26 is between rows 54 and 55, and magnetic assembly 28 is between rows 56 and 57. This arrangement positions one and only one magnetic assembly immediately adjacent each container.

Within each aperture is a corresponding aperture insert. For example in FIG. 1, aperture 52a has an aperture insert 152a into which a test tube 252a may be inserted. In combination, aperture 52a and aperture insert 152a comprise a means for accepting and holding a container such as test tube 252a. Perferably the means for accepting and holding will grasp the test tubes and allow the rack 10 to be inverted or tilted without the test tubes sliding out of the rack 10. Alternate means for accepting and holding, such as brackets attached to base 21, are envisioned to be well within the scope of the invention.

As described, rack 10 has a removable top portion 50 which holds and secures the test tubes. Top portion 50 may be removed to a separate location to facilitate the agitation of mixtures out of the influence of magnetic fields or allow easier cleaning of components.

Figure 3:
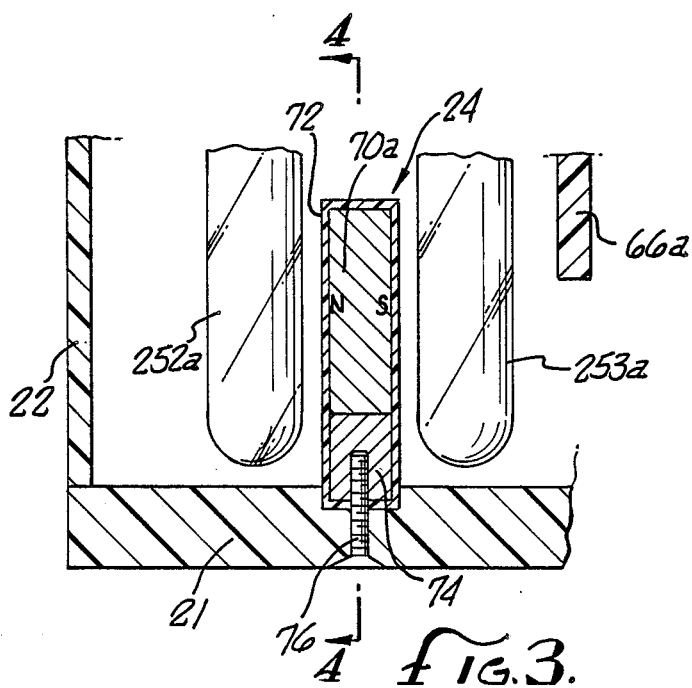
FIG. 3 is an enlarged cross section of a portion of FIG. 1.

The orientation of the magnetics will now be described with reference to FIGS. 3 and 4. FIG. 3 is an enlarged view of a portion of FIG. 1 illustrating positioning and construction details of the test tubes and the magnetic assemblies. Magnetic assembly 24 is immediately adjacent to test tube 252a and test tube 253a. Magnetic assembly 24 is comprised of a series of four magnets 70a-d which are enclosed within a protective casing 72. As viewed in FIG. 3, internally, magnetic assembly 24 has magnet 70a in the top portion thereof and a positioning plug or filler material 74 in the bottom portion thereof. The magnets 70a-d are comprised of suitable permanent magnetic material. As viewed in FIG. 3, the relative positions of the magnet 70a and the test tubes 252a, 253a are such that the magnet 70a does not extend all the way to the bottom portion of test tubes 252a, 253a. The height of the magnet 70a will be determined by the height of the liquid sample in the test tubes 252a and 253a. Filler 74, which is non-magnetic, is adjacent to the bottom portions of the test tubes 252a and 253a. Magnetic assembly 24 is attached to base 21 by screws 76, 76 which are secured into filler 74. Casing 72 is typically constructed out of a plastic material which is not magnetically active. Casing 72 also protects the magnetic material from physical and chemical damage since some magnetic materials are fragile and/or susceptible to chemical attack.

Figure 4:
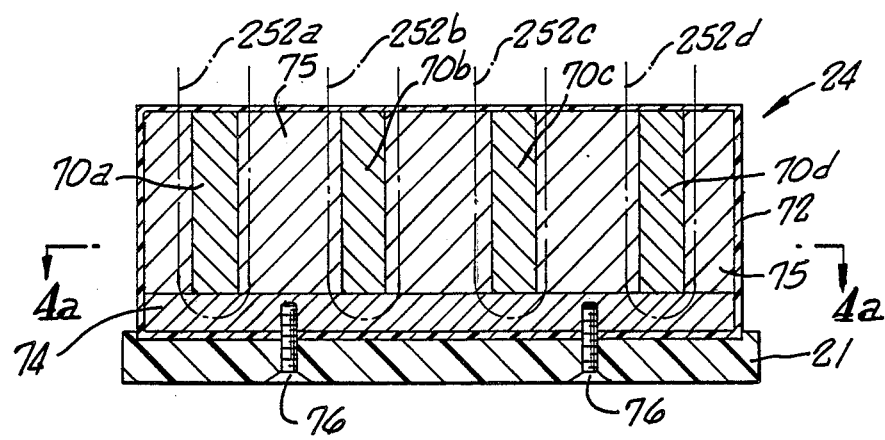
FIG. 4 is a side view.

As illustrated in FIG. 4, the magnetic assembly 24 has a series of four magnets 70a-d, one magnet corresponding and immediately adjacent to each test tube 252a-d in the row. For example, magnet 70a is immediately adjacent test tubes 252a and 253a as viewed in FIGS. 3 and 4a. The magnet 70a is preferably oriented with its magnetic field axis parallel to base 21 and perpendicular to the axes of the test tubes 252a and 253a. The specific north/south orientation of the magnet 70a within a plane parallel to the base 2 is not critical because each test tube has only one magnet acting upon it. The assembly or replacement of the magnetic assembly 24 is thereby facilitated since the installer need not determine the specific north/south orientation of the magnets 70a-d.

Figure 4A:
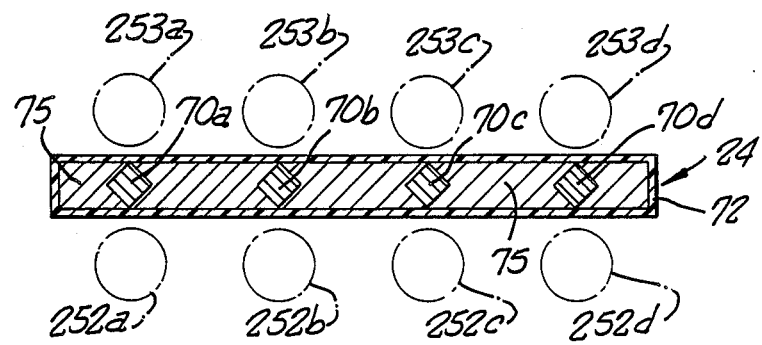
FIG. 4a is a cross section of FIG. 4.

Referring to FIG. 4a, magnets 70a-d have rectangular cross sections which are oriented to place a corner nearest the adjacent test tubes 252a-d and 253a-d. The cross sectional shape and orientation were chosen to provide superior structural integrity. Alternate cross sectional shapes and orientations for the magnets are envisioned which still include magnetic field axes parallel to the base 21. Except for the magnets such as 70a-d in the magnetic assemblies 24, 26, 28, all materials of construction are preferably non-magnetic and not magnetically active, i.e., not affected by a magnetic field. The sides 22, 22 and the front and back faces 62, 64 as well as the base 21 and the top surface 51 may be made from a clear plastic material, such as Lucite ®, to permit observation of the test tubes during testing.

The relative position of the magnet 70a, extending only part way down the side of the test tubes 252a and 253a, functions to pull the magnetically active particles to one side of the tubes. Since each test tube has only one magnet immediately adjacent thereto, particles are attracted to only one side of the tube. This method of magnetic separation differs substantially from that of existing techniques. For example in U.S. Pat. Nos. 4,438,068 and 4,272,510, the magnets are located at the bottom of the test tubes. In U.S. Pat. No. 3,985,649, the magnets are located on more than one side of the test tubes attracting particles radially outward. By locating a magnet immediately adjacent to only one side of the test tube according to the present invention, the particles to be attracted are affected by only a single magnetic field. A particle is not attracted to competing magnetic fields on more than one side of the test tube.

By drawing the particles to only one side of the test tube, a smaller surface area of the particles is subjected to agitation action as the fluid medium is flushed or decanted. The present invention also facilitates removal of fluid by aspiration since the particles are drawn to one side leaving the other side open for insertion of a removal tube.

Sometimes particles, precipitates, etc. are not attracted by the magnets and gravitate to the bottom. When the magnets are positioned at the bottom, these settling particles mix with the desired magnetically attracted ones hampering the removal of non-attracted particles. Side located magnets permit easy removal of the settling particles allowing the present invention to achieve superior results. Being subjected to only one magnetic field, the particles may move faster or be positioned more securely than if the particles were also attracted by a second magnet. The faster movement allows shortening testing time and the strong attraction permits easier rinsing which may produce superior results and shorter test times.

By locating the magnets along the side of the test tubes, the magnet may be adjacent to the test tube over a longer distance. The side positioning of magnets minimizes the maximum distance between the particles and the magnet thereby allowing the present invention to better separate a larger volume container than can methods with magnets positioned at the bottom.

Though the preferred embodiment for the magnets such as magnet 70a uses magnets which are permanent magnetic material, an electromagnetic device may be employed in place of the permanent magnetic material. Thus a magnetic separation rack and method is disclosed for performing genetic probe assays, ligand-receptor assays, immunoassays and other diagnostic assays. While embodiments and applications of this invention have been shown and described, it would be apparent to those skilled in the art that many more modifications are possible without departing from the inventive concepts herein. The invention, therefore, is not to restricted except in the spirit of the appended claims.

What is claimed:

1. A magnetic separation rack for holding a plurality of containers, said rack comprising:
   a base;
   a top surface parallel to said base and having a plurality of apertures therethrough, said apertures arranged in rows and configured to accept and hold a top portion of the containers, the apertures holding each container in a position perpendicular to said top surface with a bottom portion of each container near said base; and
   a series of magnets positioned immediately adjacent to one side of the position for each container without extending to said base, wherein the position for each container has only one magnet immediately adjacent thereto, wherein said magnets are arranged between every other row of the apertures.

2. A magnetic separation rack according to claim 1 wherein said magnets are positioned with their magnetic axes parallel to said base.

3. A magnetic separation rack for holding a plurality of test tubes, said rack comprising:

a base portion;

a plurality of test tubes;

a removable top portion having a series of apertures therethrough, said apertures configured to accept and hold the test tubes;

a magnetic means immediately adjacent a side of each test tube and extending from near said removeable top portion along the length of each test tube without extending to a bottom of the test tubes, wherein each test tube has only one magnetic means immediately adjacent thereto, wherein said apertures are arranged in rows having aisles therebetween and wherein said magnetic means are positioned in alternating aisles.

4. A magnetic separation rack according to claim 3 wherein said magnetic means are positioned with their magnetic axes parallel to said base.

* * * * *